US010335791B2

(12) United States Patent
Hayden et al.

(10) Patent No.: US 10,335,791 B2
(45) Date of Patent: Jul. 2, 2019

(54) METHODS AND DEVICES FOR SAMPLE ANALYSIS

(71) Applicant: Abbott Laboratories, Abbott Park, IL (US)

(72) Inventors: Mark A. Hayden, Ingleside, IL (US); Karen Leirs, Oud-Heverlee (BE); Elena Pérez-Ruiz, Woluwe Saint Lambert (BE); Jeroen Lammertyn, Neerijse (BE)

(73) Assignees: Abbott Laboratories, Abbott Park, IL (US); The Katholieke Universiteit Leuven, Waaistraat (BE)

( * ) Notice: Subject to any disclaimer, the term of this patent is extended or adjusted under 35 U.S.C. 154(b) by 0 days.

(21) Appl. No.: 15/873,591

(22) Filed: Jan. 17, 2018

(65) Prior Publication Data

US 2018/0207640 A1    Jul. 26, 2018

Related U.S. Application Data

(60) Provisional application No. 62/447,672, filed on Jan. 18, 2017.

(51) Int. Cl.
*B01L 3/00* (2006.01)
*G01N 33/543* (2006.01)

(52) U.S. Cl.
CPC ... *B01L 3/502784* (2013.01); *B01L 3/502707* (2013.01); *B01L 3/502792* (2013.01);
(Continued)

(58) Field of Classification Search
CPC ......... B01L 3/502784; B01L 3/502792; B01L 3/502707; G01N 33/54373
See application file for complete search history.

(56) References Cited

U.S. PATENT DOCUMENTS 7,070,921 B2    7/2006  Huang et al.
2006/0121544 A1  6/2006  Boge et al.
(Continued)

FOREIGN PATENT DOCUMENTS

WO    2016/161400    10/2016

OTHER PUBLICATIONS

Brassard et al. (2008) "Water-oil core-shell droplets for electrowetting-based digital microfluidic devices" Lab Chip 8: 1342-1349.
(Continued)

*Primary Examiner* — Melanie Brown
(74) *Attorney, Agent, or Firm* — Edward J. Baba; Shweta H. Chandra; Bozicevic, Field & Francis LLP (57) ABSTRACT

Methods for detecting target analytes utilizing an array of wells are advantageous for detection of low concentrations of target analytes. Use of an array of wells requires sealing of the wells. The methods provided herein utilize digital microfluidics to seal wells of an array with a fluid that is immiscible with the aqueous liquid present in the wells to prevent evaporation and contamination of the aqueous fluid during analysis of signals from the wells. The disclosed method include generating a biphasic droplet composed of the immiscible fluid and an aqueous fluid. The immiscible fluid present in the biphasic droplet is moved over the array of wells to seal the wells by electrically actuating the aqueous fluid present in the biphasic droplet which in turn pulls the immiscible fluid.

21 Claims, 3 Drawing Sheets

(52) U.S. Cl.
CPC .............................. *G01N 33/54373* (2013.01);
*B01L 2200/0673* (2013.01); *B01L 2200/0689*
(2013.01); *B01L 2200/12* (2013.01); *B01L*
*2300/04* (2013.01); *B01L 2300/12* (2013.01);
*B01L 2400/0427* (2013.01)

(56) References Cited

U.S. PATENT DOCUMENTS

| | | |
|---|---|---|
| 2008/0044893 A1 | 2/2008 | Pollack et al. |
| 2010/0041046 A1* | 2/2010 | Chiu ................ B01L 3/502784 435/287.2 |
| 2010/0173394 A1 | 7/2010 | Colston et al. |
| 2011/0147216 A1 | 6/2011 | Fan et al. |
| 2012/0301564 A1 | 11/2012 | Fan et al. |
| 2013/0236901 A1* | 9/2013 | Potier ................ G01N 35/1009 435/6.12 |
| 2014/0342373 A1 | 11/2014 | Viovy et al. |
| 2015/0184219 A1 | 7/2015 | Eckhardt et al. |
| 2018/0071738 A1* | 3/2018 | Blainey ............ B01L 3/502784 |

OTHER PUBLICATIONS

Chatterjee et al. (2006) "Droplet-based microfluidics with nonaqueous solvents and solutions" Lab Chip 6: 199-206.

Fan et al. (2009) "General digital microfluidic platform manipulating dielectric and conductive droplets by dielectrophoresis and electrowetting" Lab Chip 9: 1236-1242.

Kuo et al. (2003) "Electrowetting-Induced Droplet Movement in an Immiscible Medium" Langmuir 19: 250-255.

Lee et al. (2013) "On-chip micromanipulation by AC-EWOD driven twin bubbles" Sensors and Actuators A: Physical 195: 167-174.

Li et al. (2014) "Electrowetting-on-dielectrics for manipulation of oil drops and gas bubbles in aqueous-shell compound drops" Lab Chip 14: 4334-4337.

* cited by examiner

METHODS AND DEVICES FOR SAMPLE ANALYSIS

CROSS-REFERENCE TO RELATED APPLICATIONS

This application claims the benefit of U.S. Provisional Patent Application No. 62/447,672 filed Jan. 18, 2017, which application is incorporated herein by reference in its entirety.

INTRODUCTION

Digital detection using microwell arrays usually require a sealing method to close off the chambers of the array from the exterior environment. Traditionally, an immiscible fluid (e.g., oil) is spread over the array either manually or using a robotic arm coupled with a vacuum system to ensure even coverage across the array. However, manual addition of oil is undesirable since it may introduce error into the assay, due to differences in operator technique. Robotics can reduce error related to imprecision, however, it requires complex and costly engineering.

As such there is a need for improved and cost effective methods for sealing off arrays of wells, such as, those used for detection of low concentrations of analytes.

SUMMARY

Methods for using digital microfluidics (DMF) for pulling a bi-phasic droplet comprising an aqueous fluid and an immiscible fluid over the openings of an array of wells located on a DMF chip is provided. The methods disclosed herein position the immiscible fluid over the array of wells, which efficiently seals the openings of the wells. In certain embodiments, the methods disclosed herein may additionally be utilized for introducing an assay reagent (e.g., a chemical substrate) into the wells prior to sealing the wells with the immiscible fluid. In certain embodiments, the assay reagent may be present in the aqueous portion of the bi-phasic droplet.

DETAILED DESCRIPTION

Methods for using digital microfluidics (DMF) to pull a bi-phasic droplet, formed from an aqueous fluid and an immiscible fluid, in order to cover an array wells located on a DMF chip is provided. The methods disclosed herein position immiscible fluid over the array of wells, which efficiently seals the chambers. In certain embodiments, the methods disclosed herein may additionally be utilized for introducing a reagent into the wells prior to sealing with the immiscible fluid. In such embodiments, the reagent may be included in the aqueous fluid portion of the bi-phasic droplet.

Before the present invention is described in greater detail, it is to be understood that this invention is not limited to a particular embodiment described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an" and "the" include plural referents unless the context clearly dictates otherwise. Thus, for example, refer to "an electrode" includes plurality of such electrodes and reference to "a droplet" includes reference to one or more droplets and equivalents thereof known to those skilled in the art, and so forth.

All publications mentioned herein are incorporated herein by reference to disclose and describe the methods and/or materials in connection with which the publications are cited. The present disclosure is controlling to the extent there is a contradiction between the present disclosure and a publication incorporated by reference.

Methods for Sealing an Array of Wells

The present disclosure provides methods for sealing an array of wells with an immiscible fluid by electrical actuation of an aqueous phase associated with the immiscible fluid. Electrical actuation may be performed using one or more electrodes, such as, an array of electrodes, e.g., electrodes in a digital microfluidics device.

In certain embodiments, the method includes electrically actuating movement of a droplet of aqueous fluid towards a droplet of immiscible fluid by using digital microfluidics (DMF) electrodes in a DMF device such that the two droplets contact each other thereby forming a biphasic droplet comprising an aqueous phase formed by the droplet of aqueous fluid and a non-aqueous phase formed by the droplet of immiscible fluid; electrically actuating movement of the aqueous phase of the biphasic droplet by using DMF electrodes thereby pulling the non-aqueous phase present in the biphasic droplet towards an array of wells; contacting the array of wells with the aqueous phase of the biphasic droplet by actuating movement of the aqueous phase of the biphasic droplet over the array of wells by using DMF electrodes; and contacting the array of wells with the non-aqueous phase of the biphasic droplet by actuating movement of the aqueous phase of the biphasic droplet to a position adjacent the array of wells by using DMF electrodes such that the non-aqueous phase is pulled over the array of wells, wherein contacting the array of wells with the non-aqueous phase of the biphasic droplet covers the array of wells with the immiscible fluid thereby sealing the array of wells.

An immiscible fluid useful in the present methods may be any fluid that does not substantially dissolve in water-based or aqueous solution and further is not significantly actuable by electric force. In certain cases, the immiscible fluid may be a hydrophobic liquid, such as, saturated hydrocarbon, unsaturated hydrocarbon, aromatic hydrocarbon, silicone oil, per-fluorocarbon, halogen solvents, or mixtures thereof. In general immiscible fluids are non-water based or nonaqueous liquids. Immiscible fluids include but are not limited to silicone oil, mineral oil, vegetable oil, chloroform, tetrahydrofuran (THF), long-chain alcohols such as hexanol or decanol, hydrocarbons, such as decane, or any fluid/solvent that does not substantially dissolve in water-based solutions and is not significantly actuable by electric force, e.g., is not movable by electrowetting (e.g., is not directly movable by electrical force generated by DMF electrodes). In certain embodiments, the immiscible fluid may an oil such as, silicone oil or mineral oil (e.g., GE Healthcare™ IMMOBILINE™ DryStrip Cover Fluid).

In certain cases, the droplet of aqueous fluid may be generated by dispensing the droplet from a reservoir containing the aqueous fluid, where the reservoir is present in a DMF device and the dispensing is carried out by electrical actuation by DMF electrodes of the DMF device. The droplet of aqueous fluid may be a droplet of a buffer compatible with detection of an analyte or analyte related signal in the wells. In certain cases, the buffer may be a wash buffer or may include one or more reagents for generating an analyte related signal. In certain examples, the droplet of aqueous fluid may be a buffer, e.g., phosphate buffered saline (PBS) with or without additional assay reagents. The droplet of aqueous fluid may include a surfactant. The surfactant may be an ionic or a non-ionic surfactant. In certain cases, the droplet of aqueous fluid may include a non-ionic surfactant, such as, Pluronic F-68 The amount of surfactant in the aqueous fluid may range from 0.01% to 5%, e.g., 0.05%-3%, 0.05%-2%, 0.05%-1%, 0.05%-0.5%, or 0.1%-0.5%. In some cases, the reagent may be an antibody that binds directly or indirectly to the target analyte, a substrate for an enzyme present in the wells, and the like.

The droplet of immiscible fluid may be introduced into a DMF device, used to perform the present methods, by any suitable means. In certain cases, a droplet of immiscible fluid may be disposed in a gap between the substrates forming a chamber of the DMF device via an inlet in the chamber, using, capillary force or by applying pressure (e.g. applying vacuum) to release the immiscible fluid into the chamber of the DMF device.

The volume of the droplet of immiscible fluid and the droplet of aqueous fluid may be determined based on factors such as the size of the array of wells. In certain cases, the volumes may be sufficient to entirely cover or substantially entirely cover the openings of the wells of the array. In certain cases, the droplet may be deformed, e.g., flattened to increase the length and width of droplet while decreasing the height of the droplet to increase coverage of the array of wells without substantially increasing the overall volume of the droplet. In certain cases, the shape of the droplets may be controlled by using substrates having regions that differ in hydrophobicity/hydrophilicity. For example, a region of a DMF chip may be substantially hydrophilic which facilitates formation of more spherical droplets of immiscible fluid and less spherical droplets of aqueous fluid and a region of the DMF chip that contains the array of wells may include a hydrophobic surface which may lead to spreading out of the immiscible fluid over the array of wells.

A biphasic droplet may be formed by combining an aqueous droplet and a droplet of immiscible fluid, where the volumes of the two droplets are equal or substantially equal. In some cases, one or more aqueous droplets may be combined with a single droplet of immiscible fluid. In some cases, one or more droplets of immiscible fluid may be combined with a single aqueous droplet. For example, a first biphasic droplet may be formed by combining a single droplet of immiscible fluid and a single droplet of aqueous fluid, followed by combining the biphasic droplet with additional droplet(s), such as, one or more droplets of immiscible fluid and/or one or more droplets of aqueous fluid. In certain cases, such a method may be employed to control the volumes of the aqueous and/or immiscible fluids in the biphasic droplet. In certain embodiments, the biphasic droplet includes an aqueous phase in contact with a non-aqueous phase (formed by the non-aqueous immiscible fluid), where the two phases are associated with each other at an interface. A biphasic droplet of the present disclosure may also include a second interface between the non-aqueous phase and the surrounding environment (e.g. air) in the chamber of the DMF device and a third interface between the aqueous phase and the surrounding environment (e.g. air) in the chamber of the DMF device. In other words, the aqueous phase is not engulfed by the immiscible fluid and vice versa. In certain cases, the biphasic droplet may take the form of a Janus droplet, which is a spherical droplet composed of two sub-volumes occupied by two different phases and separated by a curved interface. In other cases, the biphasic droplet may not take the form of a Janus droplet and instead by have an elongated/flattened spherical shape.

Electrically actuating movement of the aqueous phase of the biphasic droplet by using DMF electrodes thereby pulling the non-aqueous phase present in the biphasic droplet towards an array of wells may be performed by energizing the DMF electrodes and exerting an electrical force on the aqueous phase of the biphasic droplet and thereby indirectly causing the movement of the immiscible (non-aqueous) phase present in the bi-phasic droplet.

Electrical actuation may then be used to drive the bi-phasic droplet to the array of wells. Since the aqueous portion of the bi-phasic droplet forms the leading portion of the droplet, the aqueous portion first contacts the array prior to the immiscible portion of the bi-phasic droplet contacting the array. The time of contact of the array with the aqueous portion and the non-aqueous portion of the bi-phasic droplet may be controlled by the movement of the bi-phasic droplet mediated by activation of the DMF electrodes. In a first embodiment, the method may include moving the aqueous portion of the bi-phasic droplet over the array at a relatively high speed to decrease the length of time the wells are exposed to the aqueous fluid. In a second embodiment, the method may include moving the aqueous portion of the bi-phasic droplet over the array of wells at a relatively slow speed or even holding the aqueous portion over the array and may include deactivating the DMF electrodes to increase the length of time the wells are exposed to the aqueous fluid. The second embodiment of the present methods may be useful for allowing diffusion of reagents present in the aqueous fluid portion of the bi-phasic droplet into the wells.

The step of contacting the array of wells with the non-aqueous phase of the biphasic droplet by actuating movement of the aqueous phase of the biphasic droplet to a position adjacent the array of wells by using DMF electrodes such that the non-aqueous phase is pulled over the array of wells may be performed by activating the DMF electrodes such that the aqueous phase of the droplet is moved off the array of wells in turn pulling the immiscible fluid portion of the biphasic droplet over the array of wells. At this point the DMF electrodes may be denergized such that the droplet remains stationary. The array of wells are effectively sealed by the immiscible fluid and can be analyzed to detect/measure an analyte related signal from the array of wells. A droplet is considered to be adjacent to an array of wells as described herein when an outer edge of the droplet is in contact with a periphery of the array of wells and/or when the droplet or at least a portion thereof is positioned over an electrode immediately adjacent to the electrode over which the array of wells is positioned such that the next cycle of activation/deactivation of electrodes can move the droplet to the array of wells. In case of a biphasic droplet, the non-aqueous phase of the droplet is adjacent the array of wells when the aqueous phase is positioned over the wells and the aqueous phase of the droplet is adjacent the array of wells when the non-aqueous phase is positioned over the wells.

Figure 1:
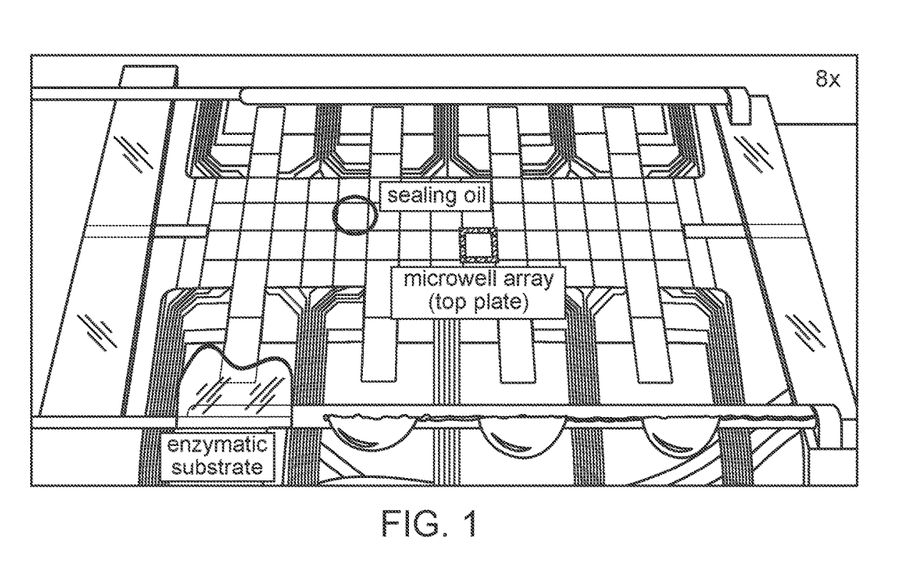
FIG. 1 illustrates a digital microfluidic device containing a droplet of immiscible fluid (e.g., sealing oil) and a droplet of aqueous fluid (e.g., enzymatic substrate) between a top plate and a bottom plate. The device includes an array of wells (marked with a square outline) in the lower surface of the top plate.

FIG. 1 shows a DMF device with a top and a bottom plate separated by a gap defining a DMF chamber. An array of individually actuable electrodes are operably connected to the device to drive movement of droplets of aqueous fluid. The device is operably connected to a reservoir containing an enzymatic substrate. A droplet of immiscible fluid (e.g., oil) is disposed in the device. The target area containing the array of wells to which the oil droplet is to be moved is marked with a square. The array of wells is located on the lower surface of the top plate with the openings of the wells in facing configuration with the space in the chamber (defined by the spaced-apart configuration of the top and bottom plates) and with the top surface of the lower plate. The DMF electrodes are positioned on the lower plate. Methods for manufacturing a DMF device with an array of wells in a facing configuration to a substrate containing DMF electrodes is disclosed in WO2016/161400, which is herein incorporated by reference. For example, FIGS. 22-26 of WO2016/161400 depict a method for making a DMF device that includes DMF electrodes on a first substrate and array of well on a second substrate, where the first and second substrates are disposed in a space-apart manner from each other and define a space therebetween and the openings of the chambers of the array of wells faces the space. The DMF device may be used in either orientation, i.e., where the first substrate is at the bottom or is at the top.

In certain cases, the array of wells may have been preloaded with microparticles (e.g., beads on which a target analyte is immobilized) or other molecules. Methods for loading microparticles into array of wells, e.g., array of wells that are located on a top plate of a DMF device and where the openings of the wells are facing down (e.g., the wells are in an upside down orientation) are disclosed in WO2016/161400 (see, e.g., FIGS. 29-30). In some cases, the wells may be loaded with magnetic beads by utilizing a magnet.

Figure 2:
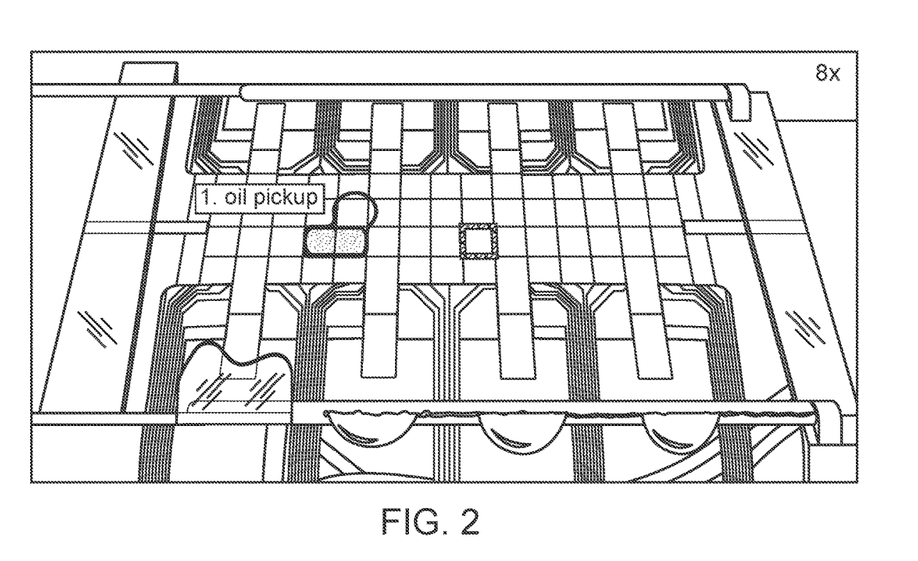
FIG. 2 illustrates movement of the aqueous droplet to the droplet of immiscible fluid and generation of a bi-phasic droplet in the digital microfluidic device.

FIG. 2 illustrates actuation of the aqueous droplet, containing an assay reagent (e.g., an enzymatic substrate), to the area of the device where the oil droplet is disposed. The oil droplet combines with the aqueous droplet creating a bi-phasic droplet in which the oil droplet is associated with the aqueous droplet such that movement of the aqueous portion causes the movement of the oil portion of the droplet.

Figure 3:
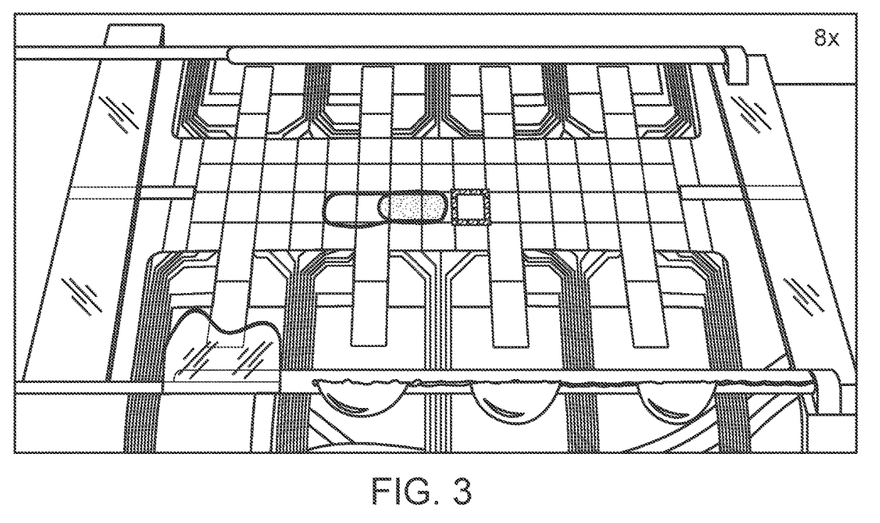
FIG. 3 illustrates movement of the bi-phasic droplet towards the array of wells in the digital microfluidic device.

FIG. 3 illustrates movement of the bi-phasic droplet towards the area in the device containing the array of wells. The bi-phasic droplet is moved using standard DMF actuation voltages on the aqueous phase of the bi-phasic droplet with the oil phase being dragged behind the aqueous phase.

Figure 4:
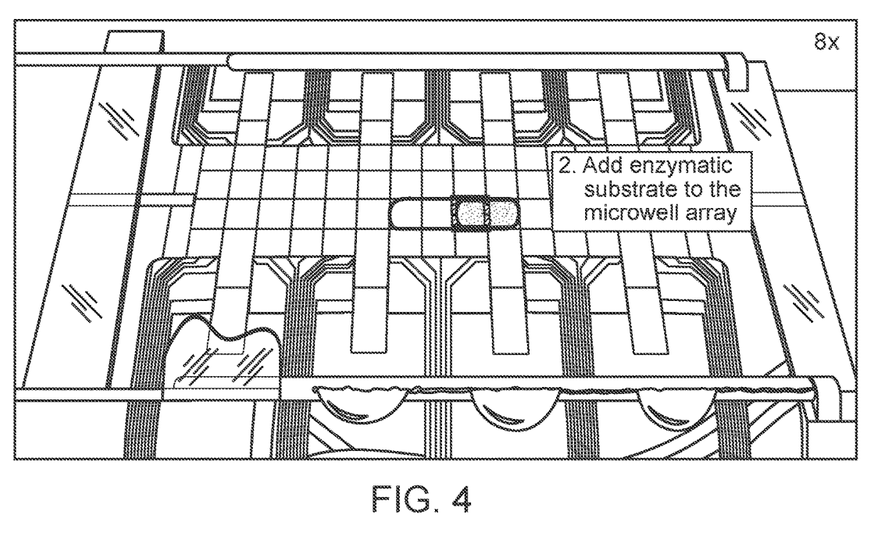
FIG. 4 illustrates positioning of part of the aqueous phase portion of the bi-phasic droplet over the array of wells with the immiscible portion of the bi-phasic droplet being positioned immediately adjacent to the array of wells.

FIG. 4 depicts positioning of the aqueous phase portion of the bi-phasic droplet at the target area. This step may optionally be used for depositing the enzymatic substrate into an array of wells present at the target area. If utilized, the bi-phasic droplet may be held at the target area for a period of time sufficient for diffusion of the enzymatic substrate into the array of wells.

Figure 5:
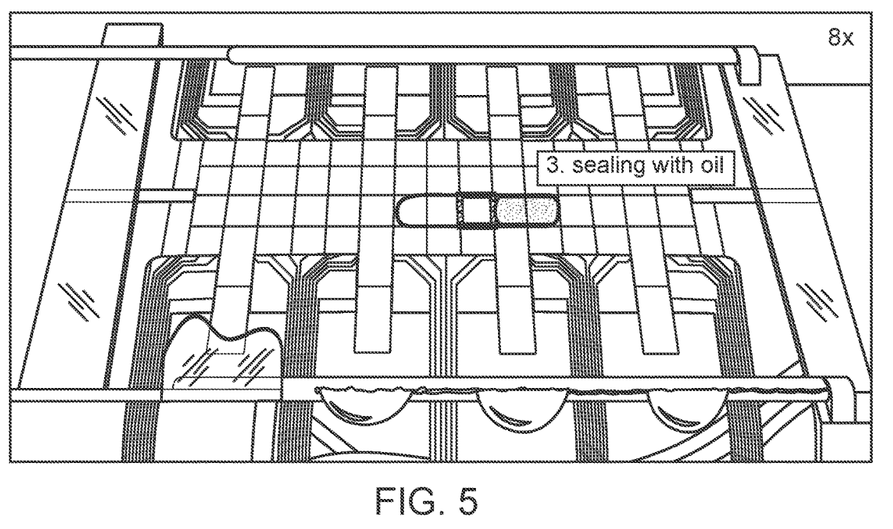
FIG. 5 illustrates positioning of part of the immiscible portion of the bi-phasic droplet over array of wells with the aqueous phase portion of the bi-phasic droplet being positioned immediately adjacent to the array of wells.

FIG. 5 illustrates movement of the biphasic droplet by actuation to allow the oil phase of the droplet to move over the target area. An array of wells included at the target area is covered with the oil. Upon positioning of the oil phase of the biphasic droplet over the target area, the driving voltage is turned off. In FIG. 5, the bi-phasic droplet is moved by a distance sufficient to move the aqueous portion of the droplet off the array and drag the immiscible portion of the bi-phasic droplet onto the array.

Figure 6:
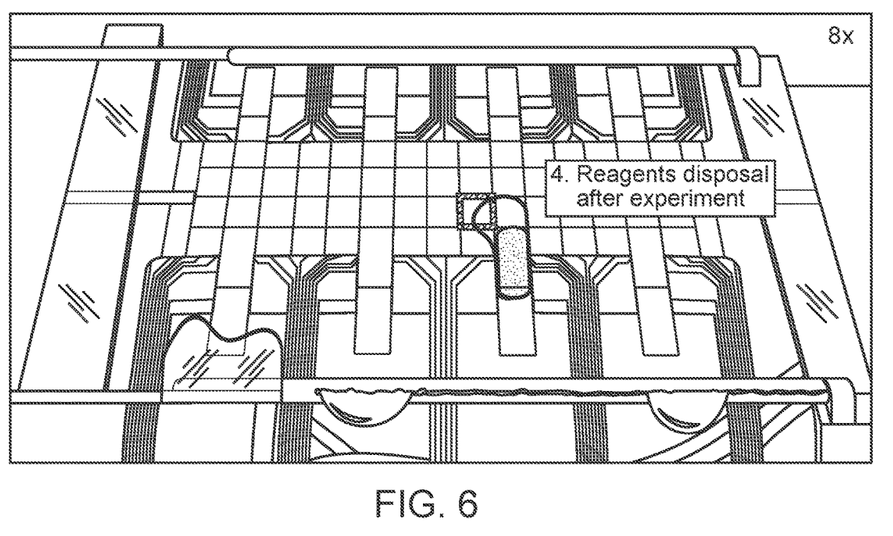
FIG. 6 illustrates movement of the bi-phasic droplet away from the array of wells and towards a disposal region.

FIG. 6 illustrates actuation of the biphasic droplet away from the target area and to a waste reservoir. Such a step may be performed optionally after the array of wells sealed with the oil has been analyzed to detect an analyte-related signal from the wells.

In certain embodiments, one or more biphasic droplets may be generated and actuated simultaneously or sequentially to cover a single array of wells or multiple arrays of wells. In certain embodiments, the method may include generating multiple bi-phasic droplets that may be positioned on a single array to entirely cover the array when a single droplet is of insufficient volume to cover the array. In certain embodiments, the DMF device may include multiple arrays of wells and individual bi-phasic droplets may be moved simultaneously or sequentially to cover the arrays.

In certain cases, the sealing of the array of wells with an immiscible liquid may performed as part of a method for detecting presence or absence of an analyte in a sample. The sample may be analyzed by first generating a liquid droplet from the sample. Such a first droplet containing or suspected of containing an analyte of interest may be manipulated by the DMF electrodes in the DMF device. In certain embodiments, method of the present disclosure may include a) providing a first liquid droplet containing an analyte of interest; (b) providing a second liquid droplet containing at least one solid support which contains a specific binding member that binds to the analyte of interest; (c) using energy to exert a force to manipulate the first liquid droplet with the second liquid droplet to create a mixture; (d) moving all or at least a portion of the mixture to the array of wells, wherein one or more wells of the array is of sufficient size to accommodate the at least one solid support; (e) adding a detectable label to the mixture either before or after moving a portion of the mixture to array of wells; (f) performing the actuating steps as described herein; (g) performing the contacting steps as described herein; and (h) detecting the analyte of interest in the wells.

In certain cases, the at least one solid support may include at least one binding member that specifically binds to the analyte of interest. In certain embodiments, the method may include adding a detectable label to the mixture after the moving at least a portion of the mixture to the array of wells. In certain cases, the aqueous droplet may include the detectable label. In certain embodiments, the detectable label may include at least one binding member that specifically binds to the analyte of interest. In certain cases, the detectable label may be a chromogen, a fluorescent compound, an enzyme, a chemiluminescent compound or a radioactive compound. In certain cases, the binding member may be a receptor or an antibody. In certain cases, the energy may be an electric actuation force. In certain cases, the first liquid droplet may be a polarizable liquid, the second liquid droplet may be a polarizable liquid, the mixture may be a polarizable liquid or both the first liquid droplet and second liquid droplet may each be polarizable polarizable liquids and directly actuable by electric force generated by DMF electrodes.

In certain cases, the solid support may be magnetic particles. The one or more wells of the array may be loaded with at least one solid support by applying a magnetic field to facilitate movement of at least one solid support into the one or more wells of the array. In certain embodiments, the actuating movement of droplets may include using electric actuation force comprising alternating current. The alternating current may have a root mean squared (rms) voltage of 10 V or more. In some embodiments, the alternating current may have a frequency of 5 KHz or more, e.g., 5 KHz-50 KHz, 5 KHz-40 KHz, 5 KHz-30 KHz, 5 KHz-20 KHz, 5 KHz-15 KHz, e.g., 5 KHz, 10 KHz, 15 KHz, or 20 KHz. In other embodiments, the alternating current may have a frequency is a radiofrequency range.

In certain embodiments, the electric actuation force generated by the DMF electrodes for moving the droplets may be an alternating current. For example, the alternating current can have a root mean squared (rms) voltage of 10V-100V, such as, 30V-70V, 30V-50V, 20V-70V, 20V-50V, 20V-100V, 30V-100V, 40V-100V, 50V-100V, 60V-100V, 70V-100V, 80V-100V, e.g., 10 V, 15 V, 20 V, 25 V, 30 V, 35V, 50V, 70V, 80V, 90V, or more.

Digital Microfluidics Devices and Systems

The methods disclosed herein may be performed on a variety of devices and associated systems that may perform the subject methods automatically or semi-automatically. In certain embodiments, a digital microfluidic device may include a first substrate and a second substrate, wherein the second substrate is positioned over the first substrate and separated from the first substrate by a gap; the first substrate comprising: a series of electrodes positioned on an upper surface of the first substrate; a first layer disposed on the upper surface of the first substrate and covering the series of electrodes; and an array of wells positioned in an area of the DMF device, where the array of wells is positioned either on the first substrate or the second substrate. In certain cases, a second layer may be disposed on an upper surface of the first layer. The first layer may be made of a material that is dielectric and hydrophobic. The array of wells may be positioned in the first layer. In other cases, the first layer may be made of dielectric layer and the second layer may be a hydrophobic layer. The array of wells may be positioned in the second layer. In certain cases, the array of wells may have a hydrophilic surface.

The first layer may be made of a material that is a dielectric and a hydrophobic material. Examples of a material that is dielectric and hydrophobic include plastic (e.g., PET or PMMA), polytetrafluoroethylene material (e.g., Teflon®) or a fluorosurfactant (e.g., FluoroPel™). The first layer may be deposited in a manner to provide a substantially planar surface. An array of wells may be positioned in a portion of the first substrate above a portion of the series of electrodes. The array of wells may be positioned in the first layer and may be hydrophobic. In certain embodiments, prior to or after fabrication of the array of wells in the first layer, a hydrophilic layer may be disposed over the first layer to provide an array of wells that have a hydrophilic surface. The space/gap between the first and second substrates may be filled with air.

In certain cases, the first layer may be a dielectric layer and a second layer of a hydrophobic material may be disposed over the dielectric layer. The array of wells may be positioned in the hydrophobic layer. Prior to or after fabrication of the array of wells in the hydrophobic layer, a hydrophilic layer may be disposed over the hydrophobic layer.

In certain cases, the second substrate may include a conductive layer that forms an electrode. The conductive layer may be disposed on a lower surface of the second substrate. The conductive layer may be covered by a first layer made of a dielectric/hydrophobic material such as plastic (e.g., PET or PMMA), as described above. In certain cases, the conductive layer may be covered by a dielectric layer. The dielectric layer may be covered by a hydrophobic layer. The conductive layer and any layer(s) covering it may be disposed across the lower surface of the second substrate. In certain embodiments, the second substrate and any layers disposed thereupon (e.g., conductive layer, dielectric layer, etc.) may be substantially transparent, at least in region overlaying the array of wells. In other cases, the array of electrodes on the first substrate may be configured as co-planar electrodes and the second substrate may not include an electrode.

In certain cases, the electrodes present in the first layer and/or the second layer may be fabricated from a substantially transparent material, such as indium tin oxide, fluorine doped tin oxide (FTC), doped zinc oxide, and the like. In certain cases, at least a portion of the first substrate and/or the second substrate may be substantially transparent to facilitate optical interrogation of the array of wells. The DMF electrode may be individually controlled such that one or more electrodes in a DMF device may be turned on while other electrodes in the DMF device can be turned off. The DMF electrodes may be co-planar or in facing configuration. For example, an array of electrodes may be present in one substrate of the device and a ground electrode disposed in the same substrate or in a second substrate disposed in a spaced apart manner from the first substrate and defining a chamber therebetween.

The devices described herein may be planar (substantially flat) and may have any shape, such as, rectangular or square, rectangular or square with rounded corners, and the like.

Droplet-based microfluidics refer to generating and actuating (such as moving, merging, splitting, etc.) liquid droplets via active or passive forces. Examples of active forces include, but are not limited to, electric field. Exemplary active force techniques include electrowetting, dielectrophoresis, opto-electrowetting, electrode-mediated, electric-field mediated, electrostatic actuation, and the like or a combination thereof. In some examples, the device may actuate liquid droplets across the upper surface of the first layer (e.g., between lower surface of the second layer and upper surface of first substrate) in the gap via droplet-based microfluidics, such as, electrowetting or via a combination of electrowetting and continuous fluid flow of the liquid droplets. Electrowetting may involve changing the wetting properties of a surface by applying an electrical field to the surface, and affecting the surface tension between a liquid droplet present on the surface and the surface. Continuous fluid flow may be used to move liquid droplets via an external pressure source, such as an external mechanical pump or integrated mechanical micropumps, or a combination of capillary forces and electrokinetic mechanisms. Examples of passive forces include, but are not limited to, T-junction and flow focusing methods. Other examples of passive forces include use of denser immiscible liquids, such as, heavy oil fluids, which can be coupled to liquid droplets over the surface of the first substrate and displace the liquid droplets across the surface. The denser immiscible liquid may be any liquid that is denser than water and does not mix with water to an appreciable extent. For example, the immiscible liquid may be hydrocarbons, halogenated hydrocarbons, polar oil, non-polar oil, fluorinated oil, chloroform, dichloromethane, tetrahydrofuran, 1-hexanol, etc. In other embodiments, electrical actuation is used for moving a bi-phasic droplet containing aqueous and immiscible phases in absence of non-electric or passive forces. The electrical actuation indirectly causes the movement of the immiscible phase by causing movement of the aqueous phase of the bi-phasic droplet which in turn pulls the immiscible phase, in absence of application of a non-electric force. Thus, in some embodiments, oil droplets may be used to push an aqueous droplet, where the oil droplet is moved by applying pressure in absence of application of an electrical force, such as, during a method for merging a sample droplet with a reagent droplet and the like.

The space between the first and second substrates may be up to 1 mm in height, e.g., 0.1 µm, 0.5 µm, 1 µm, 5 µm, 10 µm, 20 µm, 50 µm, 100 µm, 140 µm, 200 µm, 300 µm, 400 µm, 500 µm, 1 µm-500 µm, 100 µm-200 µm, etc. The volume of the droplet generated and moved in the devices described herein may range from about 10 µl to about 5 picol, such as, 10 µl-1 picol, 7.5 µl-10 picol, 5 µl-1 nL, 2.5 µl-10 nL, or 1 µl-100 nL, 800-200 nL, 10 nL-0.5 µl e.g., 10 µl, 1 µl, 800 nL, 100 nL, 10 nL, 1 nL, 0.5 nL, 10 picol, or lesser. As will be understood, the volume of the bi-phasic droplet will be the sum of the volumes of the aqueous droplet and the immiscible droplet. The volume of the bi-phasic droplet may be in the range of 10 µl to about 5 picol.

FIG. 1A of WO2016/161400 illustrates an device 10 that may be used to perform the subject methods. As described in WO2016/161400, the device 10 includes a first substrate 11 and a second substrate 12, where the second substrate 12 is positioned over the first substrate 11 and separated from the first substrate by a gap 13. As illustrated in FIG. 1A, the second substrate 12 is the same length as the first substrate 11. However, in other exemplary devices, the first substrate and the second substrate may be of different lengths. The second substrate may or may not include an electrode. The first substrate 11 includes a series of electrodes 17 positioned on the upper surface of the first substrate. A layer 18 of dielectric/hydrophobic material (e.g., Teflon which is both dielectric and hydrophobic) is disposed on the upper surface of the first substrate and covers the series of electrodes 17. An array of wells 19 is positioned in the dielectric layer 18 on the first substrate 16. In certain cases, the droplet of immiscible fluid used in the presently disclosed methods may be introduced into a proximal region of the device, e.g., close to a periphery of the device.

FIG. 2A of WO2016/161400 illustrates another exemplary digital microfluidic device 30 that may be used to perform the methods disclosed herein. The device 30 includes a first substrate 31 and a second substrate 32, where the second substrate 32 is positioned over the first substrate 31 and separated from an upper surface of the first substrate by a gap 33. The first substrate 31 includes a portion 35, where liquid droplet, such as, a sample droplet, reagent droplet, etc., is introduced onto the first substrate 31. The first substrate 31 includes a distal portion 36, towards which a liquid droplet is moved. The first substrate 31 includes a series of electrodes 37 positioned on the upper surface of the first substrate. A layer 38 of dielectric material is disposed on the upper surface of the first substrate and covers the series of electrodes 37. A layer 34 of hydrophobic material is overlayed on the dielectric layer 38. An array of wells 39 is positioned in the hydrophobic layer 34 on the distal portion of the first substrate 31. The array of wells may have a hydrophilic or hydrophobic surface.

In some examples, an aqueous droplet may be introduced into the gap via a droplet actuator (not illustrated). In other examples, an aqueous droplet or a droplet of immiscible fluid may be into the gap via a fluid inlet, port, or channel. Additional associated components of the device are not illustrated in the figures. Such components may include chambers for holding sample, wash buffers, binding members, enzyme substrates, waste fluid, etc. Assay reagents may be contained in external reservoirs as part of the device, where predetermined volumes may be moved from the reservoir to the device surface when needed for specific assay steps. Additionally, assay reagents may be deposited on the device in the form of dried, printed, or lyophilized reagents, where they may be stored for extended periods of time without loss of activity. Such dried, printed, or lyophilized reagents may be rehydrated prior or during analyte analysis.

In some examples, the first substrate can be made from a flexible material, such as paper (with ink jet printed electrodes), polymers. In other examples, the first substrate can be made from a non-flexible material, such as for example, printed circuit board, plastic or glass or silicon. In some examples, the first substrate is made from a single sheet, which then may undergo subsequent processing to create the series of electrodes. In some examples, multiple series of electrodes may be fabricated on a first substrate which may be cut to form a plurality of first substrates overlayed with a series of electrodes. In some examples, the electrodes may be bonded to the surface of the conducting layer via a general adhesive agent or solder. The second substrate may be made from any suitable material including but not limited to a flexible material, such as paper (with or without ink jet printed electrodes), polymers, printed circuit board, and the like. In other examples, the second substrate can be made from a non-flexible material, such as for example, printed circuit board, plastic or glass or silicon. In some examples, the first substrate and the second substrate are made from a material selected independently from the group consisting of glass, silicon, or plastic (e.g., Polyethylene Terephthalate (PET) or Polymethyl methacrylate (PMMA). In some examples, both substrates may be made of PMMA.

In some examples, the electrodes are comprised of a metal, metal mixture or alloy, metal-semiconductor mixture or alloy, or a conductive polymer. Some examples of metal electrodes include copper, gold, indium, tin, indium tin oxide, and aluminum. In some examples, the dielectric layer comprises an insulating material, which has a low electrical conductivity or is capable of sustaining a static electrical field. In some examples, the dielectric layer may be made of porcelain (e.g., a ceramic), polymer or a plastic (e.g., PET or PMMA). In some examples, the hydrophobic layer may be made of a material having hydrophobic properties, such as for example plastic (e.g., PET or PMMA), Teflon, poly(p-xylylene) polymers and generic fluorocarbons. In another example, the hydrophobic material may be a fluorosurfactant (e.g., FluoroPel). In embodiments including a hydrophilic layer deposited on the dielectric layer, it may be a layer of glass, quartz, silica, metallic hydroxide, or mica.

One having ordinary skill in the art would appreciate that the series of electrodes may include a certain number of electrodes per unit area of the first substrate, which number may be increased or decreased based on size of the electrodes and a presence or absence of inter-digitated electrodes. Electrodes may be fabricated using a variety of processes including, photolithography, atomic layer deposition, laser scribing or etching, laser ablation, and ink-jet printing of electrodes.

In some examples, a special mask pattern may be applied to a conductive layer disposed on an upper surface of the first substrate followed by laser ablation of the exposed conductive layer to produce a series of electrodes on the first substrate.

In some examples, the electrical potential generated by the series electrodes transfer aqueous droplets formed on an upper surface of the first layer (or the second layer when present) covering the series of electrodes, across the surface of the digital microfluidic device to be received by the array of wells. Each electrode may be capable of independently moving the droplets across the surface of the digital microfluidic device.

FIG. 3A of WO2016/161400 illustrates a side view of an exemplary integrated digital microfluidic device 100 with a droplet being moved in the gap 170. In FIG. 3A of WO2016/161400, a liquid droplet is illustrated as being actuated from the proximal portion 115 to the distal portion 130 containing the array of wells 160. A liquid droplet 180 containing a plurality of nanobeads or nanoparticles 190 is being moved across the proximal portion 115 and over to the distal portion 130 via active directional movement using the series of electrodes 145. The arrow indicates the direction of movement of the liquid droplet. Although nanobeads/nanoparticles are illustrated here, the droplet may include analyte molecules instead of or in addition to the nanobeads/nanoparticles.

In certain embodiments, the immiscible liquid used for sealing the wells and moved by electrically actuating the aqueous phase of the bi-phasic droplet may have a molecular dipole moment lower than about 0.9 D, dielectric constant lower than about 3 and/or conductivities lower than about $10^{-9}$ S m$^{-1}$. In certain embodiments, the immiscible liquid used for sealing the wells and moved by electrically actuating the aqueous phase of the bi-phasic droplet is not significantly movable by application of electric force by the DMF electrodes without association is an aqueous phase which is movable by application of electric force by the DMF electrodes. In certain embodiments, the immiscible liquid used for sealing the wells and moved by electrically actuating the aqueous phase of the bi-phasic droplet is not significantly polarizable.

FIG. 4A of WO2016/161400 illustrates a liquid droplet 180 containing nanobeads or nanoparticles 190 that has been moved to the distal portion of the device and is positioned over the array of wells 160. The droplet may be continuously moved over the array of wells or movement may be paused over the array of wells. Moving of the droplet and/or pausing the droplet over the array of wells facilitates the deposition of the nanoparticles or nanobeads 190 into the array of wells 160. The wells are dimensioned to include one nanobead/nanoparticle. In the device illustrated in FIG. 4A of WO2016/161400, the droplet is moved over the array of wells using the series of electrodes 145. Although nanobeads/nanoparticles are depicted here, droplets containing analyte molecules may also be moved in a similar manner, and by pausing the droplet containing the analyte molecules above the wells for a sufficient period of time to allow for the analyte molecules to diffuse into the wells before the immiscible fluid seals the wells. The wells are dimensioned to include one nanobead/nanoparticle. The wells can also be dimensioned to include one analyte molecule per well.

As used herein, digital microfluidics refers to use of an array of electrodes to manipulate droplets in a microfluidics device, e.g., move droplets, split droplets, merge droplets, etc. in a small space, such as the space defined between the first and second substrates. As used herein, the terms "droplet(s)" and "fluidic droplet(s)" are used interchangeably to refer to a discreet volume of liquid that is roughly spherical in shape and is bounded on at least one side by a wall or substrate of a microfluidics device. Roughly spherical in the context of the droplet refers to shapes such as spherical, partially flattened sphere, e.g., disc shaped, slug shaped, truncated sphere, ellipsoid, hemispherical, or ovoid. The volume of the droplet in the devices disclosed herein may range from about 10 µl to about 5 pL, such as, 10 µl-1 pL, 7.5 µl-10 pL, 5 µl-1 nL, 2.5 µl-10 nL, or 1 µl-100 nL, e.g., 10 µl, 5 µl, 1 µl, 800 nL, 500 nL, or lesser.

In some examples, the array of wells includes a plurality of individual wells. The array of wells may include a plurality of wells that may range from $10^9$ to 10 in number per 1 mm$^2$. In certain cases, an array of about 100,000 to 500,000 wells (e.g., femtoliter wells) covering an area approximately 12 mm$^2$ may be fabricated. Each well may measure about 4.2 µm wide×3.2 µm deep (volume approximately 50 femtoliters), and may be capable of holding a single bead/particle (about 3 µm diameter). At this density, the femtoliter wells are spaced at a distance of approx. 7.4 m from each other. In some examples, the nanowell array may be fabricated to have individual wells with a diameter of 10 nm to 10,000 nm.

In certain cases, the array of weds that are optically interrogated to measure a signal related to the amount of analyte present in the sample may have sub-femtoliter volume, femtoliter volume, sub-nanoliter volume, nanoliter volume, sub-microliter volume, or microliter volume. For example the array of wells may be array of femoliter wells, array of nanoliter wells, or array of microliter wells. In certain embodiments, the wells in an array may all have substantially the same volume. The array of wells may have a volume up to 100 µl, e.g., about 0.1 femtoliter, 1 femtoliter, 10 femtoliter, 25 femtoliter, 50 femtoliter, 100 femtoliter, 0.1 pL, 1 pL, 10 pL, 25 pL, 50 pL, 100 pL, 0.1 nL, 1 nL, 10 nL, 25 nL, 50 nL, 100 nL, 0.1 microliter, 1 microliter, 10 microliter, 25 microliter, 50 microliter, or 100 microliter.

The placement of single nanobeads/nanoparticles/analyte molecules in the wells allows for either a digital readout or analog readout. For example, for a low number of positive wells (<~70% positive) Poisson statistics can be used to quantitate the analyte concentration in a digital format; for high numbers of positive wells (>~70%) the relative intensities of signal-bearing wells are compared to the signal intensity generated from a single nanobead/nanoparticle/analyte molecule, respectively, and used to generate an analog signal. A digital signal may be used for lower analyte concentrations, whereas an analog signal may be used for higher analyte concentrations. A combination of digital and analog quantitation may be used, which may expand the linear dynamic range. As used herein, a "positive well" refers to a well that has a signal related to presence of a nanobead/nanoparticle/analyte molecule, which signal is above a threshold value. As used herein, a "negative well" refers to a well that may not have a signal related to presence of a nanobead/nanoparticle/analyte molecule. In certain embodiments, the signal from a negative well may be at a background level, i.e., below a threshold value.

The wells may be any of a variety of shapes, such as, cylindrical with a flat bottom surface, cylindrical with a rounded bottom surface, cubical, cuboidal, frustoconical, inverted frustoconical, or conical. In certain cases, the wells may include a sidewall that may be oriented to facilitate the receiving and retaining of a nanobead or nanoparticle present liquid droplets that have been moved over the well array. In some examples, the wells may include a first sidewall and a second sidewall, where the first sidewall may be opposite the second side wall. In some examples, the first sidewall is oriented at an obtuse angle with reference to the bottom of the wells and the second sidewall is oriented at an acute angle with reference to the bottom of the wells. The movement of the droplets may be in a direction parallel to the bottom of the wells and from the first sidewall to the second sidewall.

In some examples, the array of wells can be fabricated through one or more of molding, pressure, heat, or laser, or a combination thereof. In some examples, the array of wells may be fabricated using nanoimprint/nanosphere lithography.

The devices described herein may be fabricated by a number of methods. In certain cases, the methods may involve a combination of laser ablation, spray coating, roll to roll, and nanoim print lithography (NIL) to construct the first substrate, series of electrode, dielectric layer and hydrophobic layer. Exemplary methods are disclosed in WO 2016/161400, which is herein incorporated by reference.

In certain embodiments, the DMF chip may be formed using a first substrate and a second substrate, where the array of wells are located in the first substrate and used in an upside down configuration. For example, the first substrate forms a top plate of the DMF chip and includes a first surface and a second surface opposite the first surface and the second substrate forms a bottom plate of the DMF chip and includes a first surface and a second surface opposite the first surface, where the first surface of the bottom plate is in facing configuration with the second surface of the top plate and the array of wells is positioned in the second surface of the top plate. In certain embodiments, the array of wells may be positioned in a hydrophobic layer such that at least the regions in between the wells are hydrophobic. The interior of the wells may or may not be hydrophobic. In some cases, the region outside the wells is hydrophobic and the region inside the wells hydrophilic. In certain cases, the top substrate may include multiple layers. For example, the top substrate may include, from top to bottom, a layer of glass or a polymer such as a plastic (e.g., PET, cyclo olefin polymer (COP), or PMMA), a layer of conductive material forming a single electrode or an array of individually actuable electrodes (e.g., indium tin oxide (ITO)), a layer of insulating material, an array of wells positioned in the layer of insulative material. In certain cases, the layer of insulative material may be coated with a hydrophobic material which may of may not be disposed in the interior of the wells. The top substrate may be separated from the bottom substrate with a spacer that includes a cut out defining the sides of chamber, with the second surface of the top plate and the first surface of the bottom plate defining the top and bottom of the chamber. The bottom substrate may include multiple layers. For example, the bottom substrate may include, from top to bottom, a hydrophobic layer, a dielectric layer, a conductive layer forming an array of individually actuable electrodes or a single electrode, a layer of glass or a polymer such as a plastic (e.g., PET, cyclo olefin polymer (COP), or PMMA).

Any standard method may be utilized for making the top substrate, spacer and bottom substrate of such a DMF chip. For example, a PMMA, PET, or COP roll may be coated with a layer of conductive material forming a single electrode (e.g., a ground electrode). The conductive material may be coated with an insulative material and an array of wells formed in the insulative material by embossing with a drum roller having micron sized pillars followed by curing of the insulative material with UV. The insulative material may be coated with a hydrophobic material. The spacer may be created using any inert material which may be laser cut to create a desired shape of the DMF chamber. The bottom substrate may be a roll of plastic with a layer of conductive material disposed thereon. The conductive material on the bottom substrate may be laser ablated to form an array of DMF electrodes that include a plurality of individually actuable electrodes. A dielectric material may be disposed on the electrodes, followed by coating the dielectric material with a hydrophobic coating. The top substrate, the spacer, and the bottom substrate may be aligned manually, semiautomatically, or automatically and assembled into a DMF chip where the chamber defined by the top substrate, the spacer, and the bottom substrate includes a substantially hydrophobic interior defined by a hydrophobic second surface of the top substrate and a hydrophobic first surface of the bottom plate. Thus, in some embodiments, the droplets are moved in-between two hydrophobic surfaces of the DMF chamber. For assembly of the DMF chip, the second surface of the of the top substrate is placed in a facing configuration with the first surface of the bottom substrate, resulting in placement of the array of the wells in the interior of the DMF chip in an upside down configuration and facing the hydrophobic layer of the bottom substrate.

Materials used for forming the DMF chips are described herein and may be any standard material. In certain cases, the top substrate may include, from top to bottom, a layer of PET coated with a layer of conductive material (e.g. ITO), coated with a layer of insulative material such as Nalex in which an array of wells is formed by NIL, where the layer of insulative material is coated with a hydrophobic material such as, FluoroPel. In certain cases, the bottom substrate may include, from top to bottom, a layer of hydrophobic coating (e.g., FluoroPel) over a dielectric coating (e.g., Cyanoethyl Pullulan (CEP)), over a layer of aluminum (laser ablated to form an array of individually controllable electrodes), disposed over a layer of plastic (e.g., PET or PMMA) or glass.

The devices of the present disclosure may be operated manually or automatically or semi automatically. In certain cases, the devices may be operated by a processor that runs a program for carrying out the steps required for generating an analyte related signal, sealing the wells as described herein, and/or detecting the signal. As used hereon, the phrase "analyte related signal" or "analyte associated signal" refers to a signal that is indicative of presence of an analyte and is proportional to the amount of the analyte in a sample. The signal may be fluorescence, chemiluminescence, colorimetric, turbidimetric, etc. In certain cases, the read out may be digital, for example, the number of positive counts (e.g., wells) is compared to the number of negative counts (e.g., wells) to obtain a digital count.

The nanowell array may be fabricated onto the dielectric/hydrophobic layer, hydrophobic layer (if present), or hydrophilic layer (if present). One exemplary method for fabricating a nanowell array onto the hydrophobic layer of the first substrate uses thermal or ultraviolet nanoimprint lithography. As described herein, "roll-to-roll" may include the equivalent term "reel-to-reel" (R2R) and operates by moving a substrate through various components at high speeds, including, for example, rates of meters per second. Roll-to-roll assemblies facilitate the unwinding of a rolled substrate, the advancement of the substrate through the components, and the rewinding of the processed substrate into a roll.

In some examples, detection of the analyte or biological sample of interest may occur through optical signal detection. For example, shining an excitation light (e.g., laser) in order to measure the signal intensity result. In other examples, the analyte desired may be detected by measuring an optical signal emanating from each well chamber and quantified by quantifying the result. For example, the number of positive counts (e.g., wells) is compared to the number of negative counts (e.g., wells) via digital analysis. A variety of signals from the wells of the device may be detected. Exemplary signals include fluorescence, chemiluminescence, colorimetric, turbidimetric, etc.

A number of forces may be utilized to facilitate the movement of particles/beads from a droplet positioned over the array of wells into the wells. Such forces include gravity, electrical force, magnetic force, etc. Permanent magnets or electromagnets may be used as source of magnetic force. Analyte molecules may be deposited into the wells via diffusion.

Analyte Samples and Analyte Detection Assays

Any assay format may be used to generate a detectable signal which signal is indicative of presence of an analyte of interest in a sample and is proportional to the amount of the analyte in the sample. Assays such as immunoassays, clinical chem assays, cell-based assays, fluorogenic reactions, enzymatic assays, and the like may be generate an analyte related signal.

The devices provided herein may be used to measure amount of an analyte of interest in a sample. As used herein, the terms "analyte", "target analyte", "analyte of interest" refer to the analyte being measured in the methods and devices disclosed herein. An analyte may be a small molecule, peptide, protein, RNA, DNA, lipid, carbohydrate, toxin, or a cell. Samples which may assayed to determine the amount of analyte present in the sample may include biological fluid samples such as, for example, blood, plasma, serum, saliva, sweat, urine, etc.

As used herein, the terms "sample", "test sample", "biological sample" refer to fluid sample containing or suspected of containing an analyte of interest. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing the analyte may be assayed directly. The source of the analyte molecule may be synthetic (e.g., produced in a laboratory), the environment (e.g., air, soil, etc.), an animal, e.g., a mammal, a plant, or any combination thereof. In a particular example, the source of an analyte is a human bodily substance (e.g., blood, serum, plasma, urine, saliva, sweat, sputum, semen, mucus, lacrimal fluid, lymph fluid, amniotic fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, etc. The sample may be a liquid sample or a liquid extract of a solid sample. In certain cases, the source of the sample may be an organ or tissue, such as a biopsy sample, which may be solubilized by tissue disintegration/cell lysis. A sample may be processed prior to performing immunoassay on the sample. For example, the sample may be concentrated, diluted, purified, amplified, etc.

A number of immunoassay formats that generate an analyte related signal may be used. In some embodiments, a sample droplet containing the target analyte may be merged with a droplet containing magnetic beads on which a first binding member that specifically binds to the target analyte present in the sample is attached. Merging creates a single droplet which may be incubated for a time sufficient to allow binding of the first binding member to an analyte present in the sample droplet. Optionally, the single droplet may be agitated to facilitate mixing of the sample with the first binding member. Mixing may be achieved by moving the single droplet back and forth, moving the single droplet around over a plurality of electrodes, splitting a droplet and then merging the droplets. Next, the single droplet may be subjected to a magnetic force to retain the beads at a location in the device while the droplet may be moved away to a waste chamber or pad and replaced with a droplet containing a second binding member. The second binding member may be detectably labeled. The label may be any label that can be optically detected. The label may be a fluorescent label. An optional wash step may be performed, prior to adding the second binding member, by moving a droplet of wash buffer to the location at which the beads are retained using the magnetic force. The beads may or may not be resuspended in the wash buffer; a magnetic force is applied to the magnetic beads and the wash buffer is transported to a waste location. After a period of time sufficient for the second binding member to bind the analyte bound to the first binding member, the droplet containing the second binding member may be moved away while the beads are retained at the location. The beads may be washed using a droplet of wash buffer. Following the wash step, the magnetic force may be removed and a droplet containing the labeled beads which has a complex of the first binding member, analyte and the second binding member may be moved over to an array of wells. The labeled beads may be introduced into the array of wells in the detection module. The beads may introduced using gravitational force or by applying electric or magnetic force. Following an optional wash step to remove any beads not located inside the wells, the wells may be sealed by using a hydrophobic liquid, as described herein.

In another embodiment, the second binding member may be attached to a particle or a bead via a cleavable linker. Following the wash step to remove any unbound second binding member, the particle or bead attached to the second binding member may be cleaved either chemically or by photocleavage. The cleaved particles/beads may be moved to the array of well and the particles/beads present in the wells quantitated after sealing the wells as described herein. In some cases, the particles/beads attached to the second binding member may be labeled. For example, the particles/beads may be color coded or fluorescent.

In another embodiment, the second binding member may be attached to a cleavable label. Following the wash step to remove any unbound second binding member, the label attached to the second binding member may be cleaved either chemically or by photocleavage. The cleaved label may be moved to the detection module, where the label is allowed to diffuse into the wells. Following removal of any label not deposited in the wells, the wells may be sealed with a hydrophobic fluid as described herein and the label may be quantitated.

A second immunoassay format that can generate an analyte related signal may also be used. In some embodiments, a sample droplet containing the target analyte may be merged with a droplet containing labeled analyte or labeled competitor molecule to produce a single droplet. The labeled analyte or labeled competitor molecule competes with the target analyte for binding to a first binding member. The label may be any label that can be optically detected. The label may be a fluorescent label. The single droplet may be agitated to facilitate mixing which may be achieved by moving the single droplet back and forth, moving the single droplet around over a plurality of electrodes, splitting a droplet and then merging the droplets, or using SAWs, and the like. The single droplet may then be merged with a droplet containing magnetic beads on which a first binding member that specifically binds the target analyte and the labeled analyte (or the labeled competitor molecule) is attached. Merging creates a second single droplet which may be incubated for a time sufficient to allow either target analyte or labeled analyte (or the labeled competitor molecule) present in the droplet to competitively bind with the first binding member. Optionally, the second single droplet may be agitated to facilitate mixing of the target analyte-labeled analyte mixture with the first binding member. Next, the second single droplet may be subjected to a magnetic force to retain the beads at a location in the device while the droplet may then be moved away to a waste reservoir/pad and the beads may be contacted with a droplet containing a wash buffer. If a fluorescent label is used, the beads may be re-suspended in the wash buffer and then the beads may be moved over to the detection module. If the label used is an enzyme, then a magnetic force is applied to capture the magnetic beads and the wash buffer is transported to a waste location. A droplet which contains enzyme substrate may be contacted with the magnetic beads which have a complex of the first binding member, analyte and labeled analyte. Optional mixing may be performed, after which the beads may be moved over to the detection module. The labeled beads may be introduced into the array of wells. The beads may be introduced using gravitational force or by applying electric or magnetic force. Following an optional wash step to remove any beads not located inside the wells, the wells may be sealed by using an immiscible liquid, as described herein.

As will be appreciated by those in the art, the binding members will be determined by the analyte to be analyzed. Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, F(ab')$_2$ fragments, full-length polyclonal or monoclonal antibodies, antibody-like fragments, etc.), other proteins, such as receptor proteins, Protein A, Protein C, or the like. In case where the analyte is a small molecule, such as, steroids, bilins, retinoids, and lipids, the first and/or the second binding member may be a scaffold protein (e.g., lipocalins). In some cases, binding member for protein analytes may be a peptide. For example, when the target analyte is an enzyme, suitable binding members may include enzyme substrates and/or enzyme inhibitors which may be a peptide, a small molecule and the like. In some cases, when the target analyte is a phosphorylated species, the binding members may comprise a phosphate-binding agent. For example, the phosphate-binding agent may comprise metal-ion affinity media such as those describe in U.S. Pat. No. 7,070,921 and U.S. Patent Application No. 20060121544. In certain cases, at least one of the binding members may be an aptamer, a nucleic acid, such as, DNA, RNA, oligonucleotides, and the like.

In certain embodiments, the binding member binds specifically to the analyte. By "specifically bind" or "binding specificity," it is meant that the binding member binds the analyte molecule with specificity sufficient to differentiate between the analyte molecule and other components or contaminants of the test sample. For example, the binding member, according to one embodiment, may be an antibody that binds specifically to an epitope on an analyte.

What is claimed is:

1. A method for sealing an array of wells having an aqueous fluid disposed therein by disposing a layer of immiscible fluid over the array of wells, the method comprising:

actuating movement of a droplet of aqueous fluid towards a droplet of immiscible fluid by using digital microfluidics (DMF) electrodes such that the two droplets contact each other thereby forming a biphasic droplet comprising an aqueous phase formed by the droplet of aqueous fluid and a non-aqueous phase formed by the droplet of immiscible fluid;

actuating movement of the aqueous phase of the biphasic droplet by using DMF electrodes thereby pulling the non-aqueous phase present in the biphasic droplet towards an array of wells;

contacting the array of wells with the aqueous phase of the biphasic droplet by actuating movement of the aqueous phase of the biphasic droplet over the array of wells by using DMF electrodes; and contacting the array of wells with the non-aqueous phase of the biphasic droplet by actuating movement of the aqueous phase of the biphasic droplet to a position adjacent the array of wells by using DMF electrodes such that the non-aqueous phase is pulled over the array of wells, wherein contacting the array of wells with the non-aqueous phase of the biphasic droplet covers the array of wells with the immiscible fluid thereby sealing the array of wells.

2. The method of claim 1, wherein the immiscible fluid is a hydrophobic fluid that is not directly actuable by DMF electrodes and wherein the immiscible fluid is selected from the group consisting of saturated hydrocarbon, unsaturated hydrocarbon, aromatic hydrocarbon, silicone oil, per-fluorocarbon, halogen solvents, and a mixture thereof.

3. The method of claim 1, wherein the immiscible fluid is oil selected from the group consisting of silicone oil and mineral oil.

4. The method of claim 1, further comprising disposing a droplet of the immiscible fluid in a microfluidics device prior to the actuating steps, the microfluidics device comprising:

a first substrate and a second substrate, wherein the second substrate is separated from the first substrate by a gap, the first substrate comprising a plurality of DMF electrodes to generate electrical actuation forces on the droplet of aqueous fluid; and an array of wells dimensioned such that the array of wells is covered by the droplet of the immiscible fluid, wherein the array of wells is positioned on the second substrate.

5. The method of claim 4, wherein the microfluidics device includes a reservoir filled with the aqueous fluid and the method comprises generating the droplet of the aqueous fluid by actuating movement of a droplet from the reservoir.

6. The method of claim 1, wherein the aqueous fluid method comprises a substrate and wherein the method comprises contacting the array of wells with the aqueous phase of the biphasic droplet for a period of time sufficient for diffusion of the substrate to the array of wells.

7. The method of claim 4, wherein the method comprises analyzing the array of wells to detect presence of an analyte-related signal.

8. The method of claim 1, wherein at least the first or the second substrate is substantially transparent to facilitate detection of presence of the analyte-related signal.

9. The method of claim 1, wherein actuating movement of droplets comprises using electric actuation force comprising alternating current.

10. The method of claim 9, wherein the alternating current has a root mean squared (rms) voltage of 10 V or more.

11. The method of claim 1, wherein method comprises:
(a) providing a first liquid droplet containing an analyte of interest;
(b) providing a second liquid droplet containing at least one solid support which contains a specific binding member that binds to the analyte of interest;
(c) using energy to exert a force to manipulate the first liquid droplet with the second liquid droplet to create a mixture;
(d) moving all or at least a portion of the mixture to the array of wells, wherein one or more wells of the array is of sufficient size to accommodate the at least one solid support;
(e) adding a detectable label to the mixture either before or after moving a portion of the mixture to the array of wells;
(f) performing the actuating steps of claim 1;
(g) performing the contacting steps of claim 1; and
(h) detecting the analyte of interest in the wells.

12. The method of claim 11, wherein the at least one solid support comprises at least one binding member that specifically binds to the analyte of interest.

13. The method of claim 11, further comprising adding a detectable label to the mixture after the moving at least a portion of the mixture to the array of wells.

14. The method of claim 13, wherein the detectable label is present in the aqueous droplet.

15. The method of claim 11, wherein the detectable label comprises at least one binding member that specifically binds to the analyte of interest.

16. The method of claim 11, wherein the detectable label comprises a chromogen, a fluorescent compound, an enzyme, a chemiluminescent compound or a radioactive compound.

17. The method of claim 11, wherein the binding member is a receptor or an antibody.

18. The method of claim 11, wherein the energy is an electric actuation force.

19. The method of claim 11, wherein the first liquid droplet is a polarizable liquid, the second liquid droplet is a polarizable liquid, the mixture is a polarizable liquid or both the first liquid droplet and second liquid droplet are each polarizable liquids and directly actuable by electric force generated by DMF electrodes.

20. The method of claim 11, wherein the solid support comprises magnetic particles.

21. The method of claim 11, wherein one or more wells of the array are loaded with at least one solid support by applying a magnetic field to facilitate movement of at least one solid support into the one or more wells of the array.

* * * * *